United States Patent
Lin et al.

(10) Patent No.: US 7,314,960 B1
(45) Date of Patent: Jan. 1, 2008

(54) CATALYTIC SYNTHESIS OF OXYGENATE FROM ALCOHOL

(75) Inventors: Sheng-Diann Lin, Tao-Yuan (TW); Ting-Chou Hsiao, Tao-Yuan (TW)

(73) Assignee: Yuan Ze University, Tao-Yuan (TW)

( * ) Notice: Subject to any disclaimer, the term of this patent is extended or adjusted under 35 U.S.C. 154(b) by 0 days.

(21) Appl. No.: 11/536,633

(22) Filed: Sep. 28, 2006

(51) Int. Cl.
*C07C 45/29* (2006.01)
(52) U.S. Cl. ............... 568/383; 568/412; 568/449; 568/494; 568/698
(58) Field of Classification Search ............ 568/383, 568/412, 449, 494, 698
See application file for complete search history.

(56) References Cited

U.S. PATENT DOCUMENTS

2004/0242917 A1* 12/2004 Inui et al. ............ 560/205

* cited by examiner

*Primary Examiner*—Elvis O. Price
(74) *Attorney, Agent, or Firm*—WPAT, P.C.; Justin I. King

(57) ABSTRACT

The present invention discloses a method for catalytic synthesis of oxygenate from alcohol. At first, a feeding material comprising at least one alcohol is provided. Next, a copper-containing catalyst is provided and the catalyst further comprises at least one metal element selected from the group consisting of the following: zinc, magnesium, and aluminum elements. Following that, a catalytic reaction of the feeding material over the copper-containing catalyst is carried out to synthesize at least one oxygenate.

22 Claims, 3 Drawing Sheets

CATALYTIC SYNTHESIS OF OXYGENATE FROM ALCOHOL

BACKGROUND OF THE INVENTION

1. Field of the Invention

The present invention is generally related to a method for catalytic synthesis of oxygenate, and more particularly to a method for catalytic synthesis of carbon-chain-lengthened oxygenate from at least one alcohol.

2. Description of the Prior Art

At present, methanol raw material is low cost and its source does not rely on petroleum. Much attention has been attracted in developing a novel synthetic process from methanol, especially for an era having a sky-high oil price. Traditionally, the processes having methanol as the reactant comprise: methanol-to-hydrocarbon (MTH) process, methanol-to-gasoline (MTG) process, methanol-to-olefin (MTO) process and so forth. The products of these processes are long carbon-chain compounds without oxygen, such as alkanes, aromatics, or olefins. Although there are processes involving synthesis of esters and ethers from alcohols, there is few report on the synthesis of carbon-chain-lengthened oxygenate. In addition, the catalyst commonly used for the MTH, MTG, or MTO process is zeolite, at an operating temperature beyond 623 K. These processes are energy consuming and not economical. In light of the above background, a new catalyst and catalytic pathway to provide a method for catalytic synthesis of carbon-chain-lengthened oxygenate from alcohol are still needed to be applied in petroleum substitutes, additives, or other special chemicals so as to meet the requirements of energy saving processes.

SUMMARY OF THE INVENTION

In view of the above background, the present invention provides a new method for catalytic synthesis of carbon-chain-lengthened oxygenate from alcohol, in order to meet industrial requirements.

One object of the present invention is to synthesize carbon-chain-lengthened (for example two times of the carbon number) oxygenate, such as aldehydes, ketones, esters, ethers, or alcohols, from low carbon alcohol over a copper-containing catalyst. Especially, catalytic synthesis of $C_2$-$C_9$ oxygenate from methanol can be achieved. The raw material used is low carbon alcohol which is basic chemical product. Therefore, needs for petroleum raw material can be lessened.

Another object of the present invention is to provide a process with low catalytic temperature. For example, in the case of using methanol as the reactant, the catalyst according to the present invention can be operated at temperature of 473-523 K. which is lower than that of the existing similar technique, such as MTH, MTG, or MTO process. Therefore, the present invention does have the economic advantages for industrial applications.

Accordingly, the present invention discloses a method for catalytic synthesis of oxygenate from alcohol. At first, a feeding material comprising at least one alcohol is provided. Next, a copper-containing catalyst is provided and the catalyst further comprises at least one metal element selected from the group consisting of the following: zinc, magnesium, and aluminum elements. Following that, a catalytic reaction of the feeding material over the copper-containing catalyst is carried out to synthesize at least one oxygenate.

DESCRIPTION OF THE PREFERRED EMBODIMENTS

Figure 1:
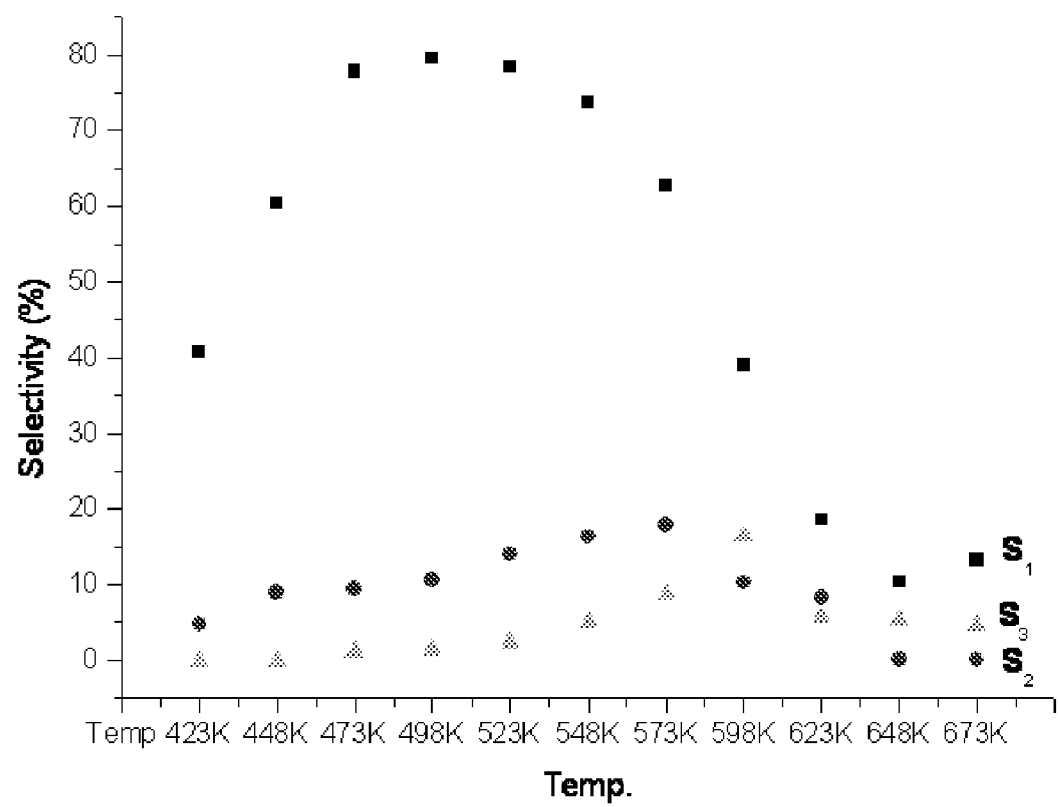
FIG. 1 is a diagram showing the pathway selectivity of the catalytic reaction over a commercial $Cu/ZnO/Al_2O_3$ catalyst at WHSV=$2h^{-1}$ and ethanol partial pressure 200 torr according to a second embodiment of the present invention.

What is probed into the invention is a method for catalytic synthesis of oxygenate from alcohol. Detail descriptions of the processes and compositions will be provided in the following in order to make the invention thoroughly understood. Obviously, the application of the invention is not confined to specific details familiar to those who are skilled in the art. On the other hand, the common compositions or processes that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Generally, solid catalyst comprises three components: primary component, secondary component (secondary catalyst), and catalyst support. The primary component provides the major functionality of catalyst, such as transition metal or metal oxides. The secondary component adjusts the functionality of catalyst to assist the primary component in accomplishing perfect catalysis. The catalyst supports are generally high-temperature-durable and stable porous metal oxides having huge surface area to disperse the primary and secondary components so as to promote contacts between reactants and the primary and secondary components. The primary and secondary components are supported on the catalyst support steadily so that the catalyst support can provide heat conduction and mechanical strength to prevent loss of catalyst.

The primary and secondary components of the catalyst have activator structures which are major sources to provide chemical adsorption. The primary and secondary components of the catalyst cooperate with each other to control selectivity of the catalyst and lower the activation energy of the reactant so as to carry out the chemical transformation of reactant molecules to become product molecules. After a cycle of chemical change completed by the primary and secondary components, the product molecules are desorbed and released. Reactant molecules proceed through adsorption and chemical transformation repeatedly to maintain the lifetime of the catalyst. Besides, the catalyst support having large surface area is an important component to assist the primary and secondary components in bringing out the function.

In general, while preparing catalyst, the primary and secondary components and support are designed according to experience, reaction characteristics, and properties of material. After the precursors of the above components, such as nitrates, are mixed and dissolved, they can be co-impregnated or co-precipitated, dried, then calcined in air to thereby decompose into oxides. Alternatively, the precursors can be sequentially impregnated or precipitated. They can be reduced to metallic state, if necessary. The calcination process is very important in catalyst preparation. Through the calcination process, the organic or anion parts of salts like nitrates, carbonates, or acetates are decomposed and oxidized into oxides. In addition, vaporizable inclusion can be removed and catalyst can have clean surfaces so as to have adsorption capability. Porous structure is also created to provide huge surface area. The common support comprises porous aluminum oxide, silicon oxide, zirconium oxide, titanium oxide, zinc oxide, magnesium oxide or activated carbon.

In a first embodiment of the present invention, a method for catalytic synthesis of oxygenate from alcohol is disclosed. At first, a feeding material comprising at least one alcohol is provided. The alcohol is low carbon alcohol and its carbon number is less than or equal to 4. When the mentioned feeding material is in vapor phase, the oxygen concentration of the feeding material is less than or equal to 5 vol %, and 3 vol % is preferred. In a preferred example of this embodiment, the feeding material does not contain oxygen. Next, a copper-containing catalyst is provided and the catalyst further comprises at least one metal element selected from the group consisting of the following: zinc, magnesium, and aluminum elements. Following that, a catalytic reaction of the feeding material over the copper-containing catalyst is carried out to synthesize at least one oxygenate. The operating temperature is controlled between 423 K. and 723 K. Preferable catalytic temperature ranges from 473 K. to 523 K. In a preferred example, the carbon number of the at least one oxygenate is lager than that of the alcohol. Moreover, the weight-hourly-space-velocity of the feeding material in the catalytic reaction is from 0.01 to 2 $h^{-1}$.

The copper-containing catalyst can be, for example, Cu—Zn, Cu—Al, Cu—Zn—Mg, Cu—Zn—Al, Cu—Mg—Al, Cu—Zn—Mg—Al metal or metal oxide; or supported copper catalyst using aluminum oxide or silicon oxide as the support. The primary component of the supported copper catalyst is copper metal or copper metal oxide while the secondary component is Zn and/or Mg and/or Al metal or metal oxide. Furthermore, the method for preparing the catalyst comprises co-precipitation, impregnation, electroless plating, sol-gel method, and other methods for copper catalyst that are known to those who are skilled in the art.

EXAMPLE 1

Method for Preparing Cu—Zn—Mg—Al Based Catalyst

Dissolve copper nitrate and zinc nitrate compounds in water and use impregnation method to let copper and zinc impregnated on the flake structure of Mg—Al. Next, dry by vacuum. Carry out oxygen calcinations at 673 K. to form Cu—Zn—Mg—Al based catalyst. Set the catalyst in a dry box for use.

In a second embodiment of the present invention, a method for catalytic synthesis of oxygenate from alcohol is disclosed. At first, a copper-containing catalyst is provided. The selection and preparation methods are the same as those in the first embodiment. Next, a reduction process for the copper-containing catalyst is carried out. Due to large surface area of the catalyst, oxygen gas in air is very easy to adsorb on the catalyst and thus regeneration or reduction treatment of the catalyst is required before use. For example, the reduction process can be performed under environment with hydrogen gas and temperature of 473 K.-573 K. Finally, the catalytic reaction of a feeding material over the reduced copper-containing catalyst is carried out to synthesize at least one oxygenate. In a preferred example, the carbon number of the at least one oxygenate is lager than that of the alcohol. The selection for alcohol, the feeding material, the weight-hourly-space-velocity of the feeding material, and the catalytic temperature range are the same as those in the first embodiment.

EXAMPLE 2

Three-component Catalyst

The reaction pathway of the catalytic synthesis of oxygenate from alcohol according to the present invention comprises the following three species:

$S_1$. alcohol-aldehyde or ketone
$S_2$. alcohol-ester or ether
$S_3$. alcohol-oxygenate (condensation, carbon chain lengthened).

Figure 2:
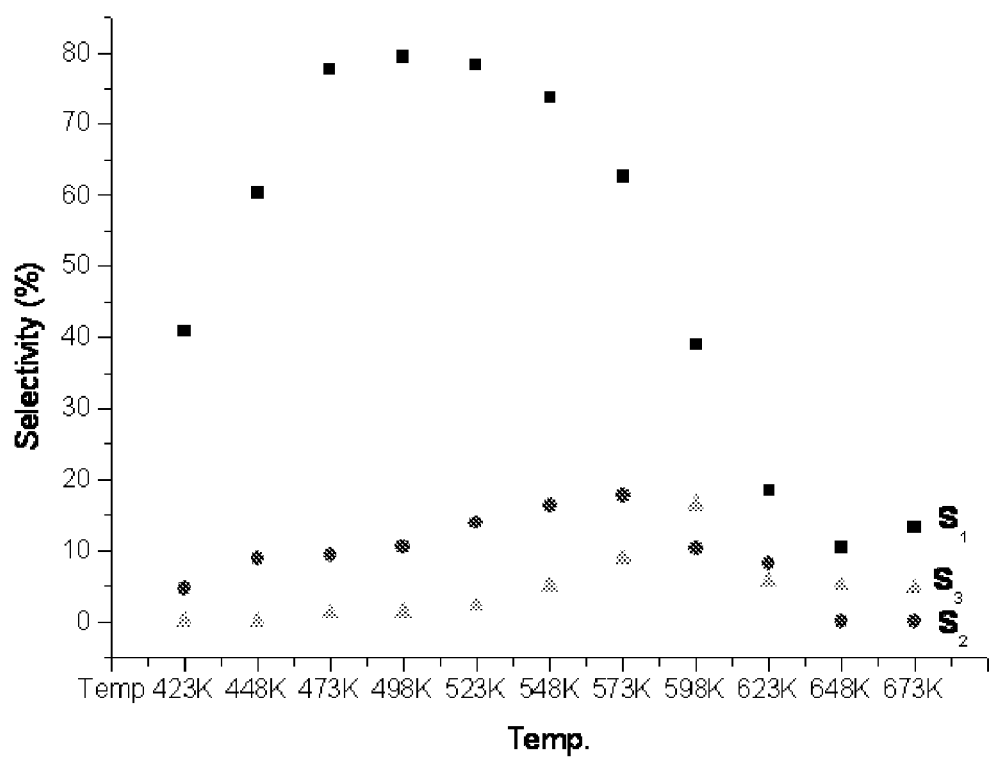
FIG. 2 is a diagram showing the pathway selectivity of the catalytic reaction over another commercial $Cu/ZnO/Al_2O_3$ catalyst at WHSV=$2h^{-1}$ and ethanol partial pressure 200 torr according to a second embodiment of the present invention.

The oxygenate synthesized by the third mechanism $S_3$ may have a continual side-reaction, such as hydrogen addition reaction to form glycol (Its carbon number is larger than alcohol initiator.) or hydrogen addition and dehydration reaction to form alcohol, aldehyde, or ketone (Its carbon number is larger than alcohol initiator.). As the reactant is ethanol, FIGS. 1 and 2 shows the diagrams of the pathway selectivity of the catalytic reaction over two commercial $Cu/ZnO/Al_2O_3$ catalysts, respectively.

EXAMPLE 3

Four-component Catalyst

Cu—Zn—Mg—Al based catalyst after hydrogen reduction treatment is used to catalyze the synthesis of carbon-chain-lengthened oxygenate from methanol under the conditions that the temperature is 523 K., the methanol partial pressure is 200 torr, and the weight-hourly-space-velocity (WHSV) is $0.2h^{-1}$. The selectivity to condensation products is at least 25%. The detailed reference is shown in Table 1.

TABLE 1
Product analysis of methanol reaction catalyzed over Cu—Zn—Mg—Al four-component catalyst
| $C_2$-$C_9$ | Total % | Aldehyde or Ketone (%) | Ester (%) | Ether (%) | Alcohol (%) |
|---|---|---|---|---|---|
| $C_2$ | 12.1 | 2.1  | 2.2 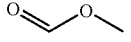 | 7.4  | 0.4  |
| $C_3$ | 12.9 | 12.9 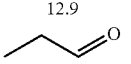 | — | — | — |
| $C_4$ | 3.7 | 3.0 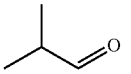 | — | — | 0.7 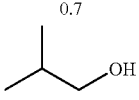 |
| $C_5$ | 5.7 | 3.3 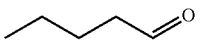 | 0.6 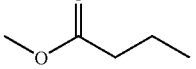 | 1.8 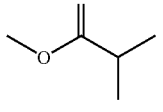 | — |
| $C_6$ | 6.1 | 3.0  | 1.1 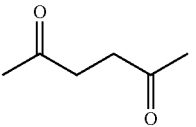 | 2.0 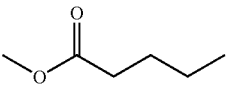 | — |
| $C_7$ | 15.9 | 12.5 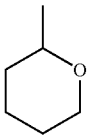 | 0.5 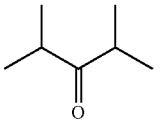 | 1.7 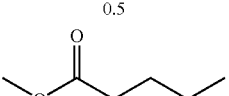 | 1.2 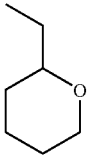 |
| $C_8$ | 14.4 | 14.4 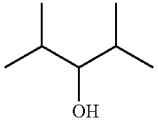 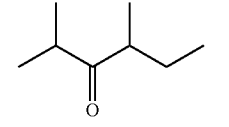 | — | — | — |
| $C_9$ | 26.1 | 25.1 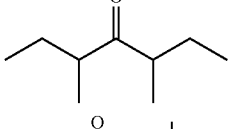 | — | 1.0 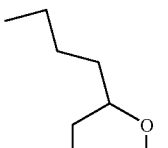 | — |

TABLE 1-continued

Product analysis of methanol reaction catalyzed over
Cu—Zn—Mg—Al four-component catalyst

| $C_2$-$C_9$ | Total % | Aldehyde or Ketone (%) | Ester (%) | Ether (%) | Alcohol (%) |
|---|---|---|---|---|---|
| (structures shown) | | | | | |
| Total | | 76.3 | 4.4 | 13.9 | 2.3 |

EXAMPLE 4

$C_3$ Alcohol as the Reactant

Figure 3:
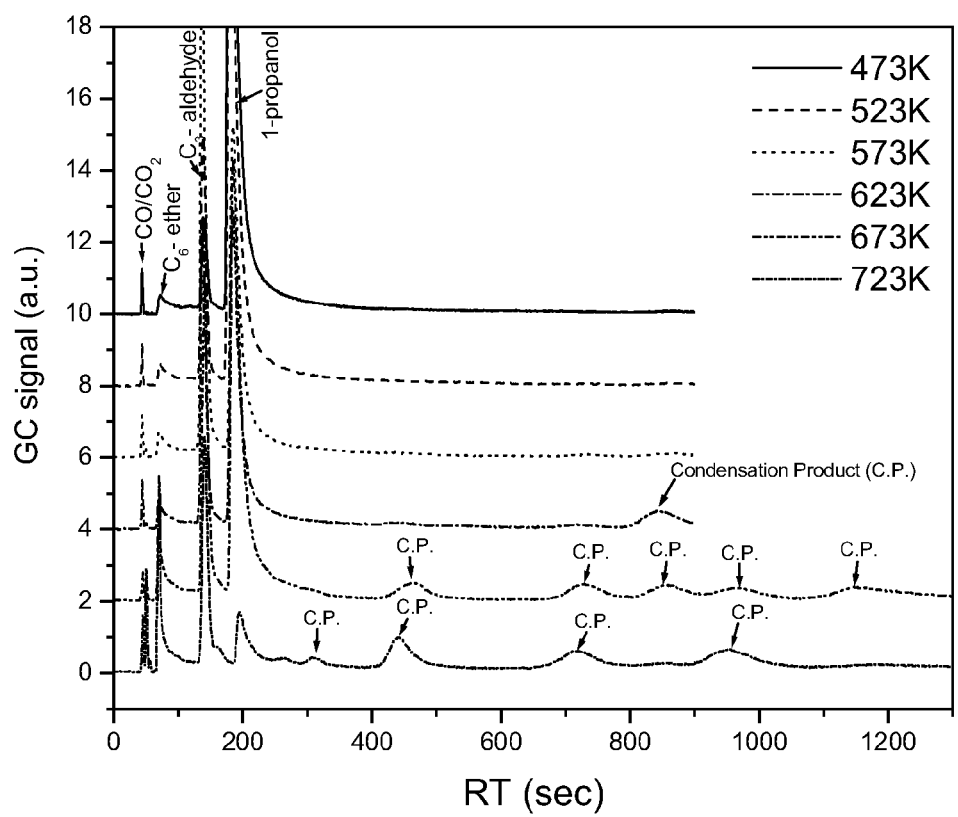
FIG. 3 is a gas chromatographic analysis diagram of the products of catalyzing n-propanol over Cu—Zn—Mg—Al based catalyst at different temperatures according to a second embodiment of the present invention.

FIG. 3 is a gas chromatographic analysis diagram of the products of catalyzing n-propanol over Cu—Zn—Mg—Al four-component catalyst at temperature of 473-723 K. It is found that the major product contains ether, three-carbon aldehyde and higher-carbon condensation products; the condensation products increase along with the increase of catalytic temperature.

In the above preferred embodiments, the present invention provides a method for catalytic synthesis of carbon-chain-lengthened oxygenate, including aldehyde, ketone, ester, ether, or alcohol from low carbon alcohol over a copper based catalyst. Especially, catalytic synthesis of $C_2$-$C_9$ oxygenate from methanol can be achieved. In addition, the present invention provides a process with low catalytic temperature. For example, in the case of using methanol as the reactant, the catalyst according to the present invention can be operated at temperature of 473-523 K. which is lower than that of the existing similar technique, such as MTH, MTG, or MTO process. Therefore, the present invention does have the economic advantages for industrial applications.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A method for catalytic synthesis of oxygenate from alcohol, comprising:
   providing a feeding material comprising at least one alcohol;
   providing a Cu—Zn—Mg—Al based catalyst; and
   carrying out a catalytic reaction of said feeding material over said Cu—Zn—Mg—Al based catalyst, so as to synthesize at least one oxygenate.

2. The method according to claim 1, wherein said alcohol is low carbon alcohol having the carbon number lower than or equal to 4.

3. The method according to claim 1, wherein the oxygen concentration of said feeding material is less than or equal to 5 vol %.

4. The method according to claim 1, wherein said feeding material does not contain oxygen.

5. The method according to claim 1, wherein the method for preparing said copper-containing catalyst comprises one of the following group: co-precipitation, impregnation, electroless plating, and sol-gel method.

6. The method according to claim 1, wherein said copper-containing catalyst is alumina-supported copper-based catalyst.

7. The method according to claim 6, wherein said feeding material is methanol and the main composition of the synthesized product is $C_2$-$C_9$ oxygenate.

8. The method according to claim 1, wherein the temperature of said catalytic reaction ranges between 423 K. and 623 K.

9. The method according to claim 1, wherein the weight-hourly-space-velocity of said feeding material in said catalytic reaction is from 0.01 to $2h^{-1}$.

10. The method according to claim 1, wherein the carbon number of the at least one oxygenate is lager than that of said alcohol.

11. A method for catalytic synthesis of oxygenate from alcohol, comprising:
    providing a Cu—Zn—Mg—Al based catalyst;
    carrying out a reductive reaction for said Cu—Zn—Mg—Al based catalyst; and
    carrying out a catalytic reaction of a feeding material containing at least one alcohol over said reduced Cu—Zn—Mg—Al based catalyst, so as to synthesize at least one oxygenate.

12. The method according to claim 11, wherein the method for forming said copper-containing catalyst comprises one of the following group: co-precipitation, impregnation, electroless plating, and sol-gel method.

13. The method according to claim 11, wherein said copper-containing catalyst is alumina-supported copper-based catalyst.

14. The method according to claim 11, wherein said feeding material is methanol and the main composition of the synthesized product is $C_2$-$C_9$ oxygenate.

15. The method according to claim 11, wherein said reductive reaction is performed under the environment containing hydrogen gas.

16. The method according to claim 11, wherein the temperature of said reductive reaction ranges between 473 K. and 573 K.

17. The method according to claim 11, wherein the temperature of said catalytic reaction ranges between 423 K. and 623 K.

18. The method according to claim 11, wherein said alcohol is low carbon alcohol having the carbon number lower than or equal to 4.

19. The method according to claim 11, wherein the oxygen concentration of said feeding material is less than or equal to 5 vol %.

20. The method according to claim 11, wherein said feeding material does not contain oxygen.

21. The method according to claim 11, wherein the weight-hourly-space-velocity of said feeding material in said catalytic reaction is from 0.01 to $2h^{-1}$.

22. The method according to claim 11, wherein the carbon number of the at least one oxygenate is lager than that of said alcohol.

* * * * *